(12) United States Patent
Kertesz et al.

(10) Patent No.: US 7,608,731 B2
(45) Date of Patent: Oct. 27, 2009

(54) PHENYLACETIC ACID COMPOUNDS

(75) Inventors: Denis John Kertesz, Mountain View, CA (US); Michael Martin, San Francisco, CA (US); Wylie Solang Palmer, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/977,262

(22) Filed: Oct. 23, 2007

(65) Prior Publication Data
US 2008/0108810 A1    May 8, 2008

Related U.S. Application Data

(62) Division of application No. 11/105,990, filed on Apr. 14, 2005, now Pat. No. 7,291,729.

(60) Provisional application No. 60/562,650, filed on Apr. 15, 2004.

(51) Int. Cl.
*C07C 205/00*    (2006.01)
(52) U.S. Cl. .................................. 560/21; 562/434
(58) Field of Classification Search .................. 560/21; 562/434
See application file for complete search history.

(56) References Cited

U.S. PATENT DOCUMENTS 7,189,718 B2 *  3/2007  Dunn et al. ............... 514/236.5
2004/0198736 A1  10/2004  Dunn et al.

OTHER PUBLICATIONS

D. Boger et al., *Design, synthesis, and biological evaluation of fluoronitrophenyl substituted folate analogues as potential inhibitors of GAR transformylase and AICAR transformylase*, Bioorg. Med. Chemistry Letters (2000) vol. 10: 1471-1475.
F. Terrier, *Nucleophilic Aromatic Displacement: The Influence of the Nitro Group* VCH Publishers, New York, NY (1991) pp. 190-201.
P. M. O'Neill et al., *The Effect of Fluorine Substitution on the Metabolism and Antimalarial Activity of Amodiaquine*, J. Med. Chem. (1994) vol. 37:1362-1370.
W. C. Lumma, Jr. et al., *Piperazinylquinoxalines with central serotoninmimetic activity*, J. Med. Chem. (1981) vol. 24:93-101.

K. Schank, *Synthetic Applications of Diazonium Ions in The Chemistry of the Diazonium and Diazo* Group, S. Patai (ed), Part 2, (1978) John Wiley & Sons, New York, NY, pp. 647-648.
M. P. Doyle et al, *Alkyl nitrite-metal halide deamination reactions. 2. Substitutive deamination of arylamines by alkyl nitrites and copper(II) halides. A direct and remarkably efficient conversion of arylamines to aryl halides*, J. Org. Chem. (1977) vol. 42:2426-2431.
S. Oae et al. *Direct Conversion of Arylamines to the Halides by Demaination with Thionitrite or Related Compounds and Anhydrous Copper (II) Halide*, Bull. Chem. Soc. Japan (1980) vol. 53:1065-1069.
H. Suschitzky, *The Balz-Schiemann reaction*, Adv. Fluorine Chem. (1965) vol. 4:1-30.
R. A. Massy-Westropp, R. A. and M. F. Price, *The Synthesis of 5-Oxo-2,5-dihydrofuran-2-ylideneacetic Acid*, Aust. J. Chem. (1980) vol. 33: 333-341.

* cited by examiner

*Primary Examiner*—Porfirio Nazario Gonzalez
(74) *Attorney, Agent, or Firm*—Brian L. Buckwalter

(57) ABSTRACT

The present invention provides a process for the preparation 6-[3-(hetero)aryloxy-2-fluoro-benzyl]-2H-pyridazin-3-one compounds 1 where R2 is an optionally substituted aryl or an optionally substituted heteroaryl, $R^6$ is $NO_2$, $NH_2$, alkyl, halogen, or a function group readily derived therefrom and $R^{4c}$ is

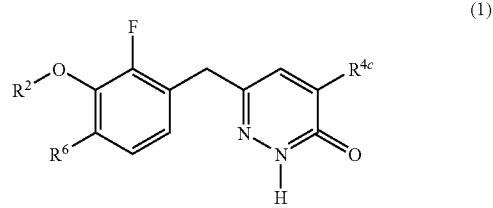

(1)

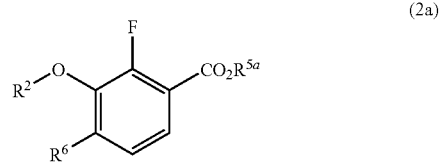

(2a)

hydrogen or alkyl. There also is provided a process for the preparation of phenylacetic acid compounds 2, wherein $R^2$ and $R^6$ are as defined previously and $R^{5a}$ is hydrogen or alkyl, which are useful for the preparation of pyridazinone compounds.

1 Claim, No Drawings

PHENYLACETIC ACID COMPOUNDS

CROSS REFERENCE TO RELATED APPLICATIONS

This application is a divisional application of U.S. application Ser. No. 11/105,990 filed Apr. 14, 2005 now U.S. Pat. No. 7,291,729 which claims the benefit of priority to U.S. Ser. No. 60/562,650 filed Apr. 15, 2004, which is hereby incorporated by reference in its entirety.

FIELD OF THE INVENTION

The present invention relates to a process for the preparation of 6-(2-fluoro-3-(hetero)aryl-benzyl)-4-alkyl-2H-pyridazin-3-one (1; $R^{4c}$ is alkyl) and 6-(2-fluoro-3-(hetero)aryloxy-benzyl)-2H-pyridazin-3-one compounds (1; $R^{4c}$ is hydrogen) compounds where $R^1$, $R^2$, $R^{4a}$, $R^{4c}$ and $R^6$ are defined below. The invention also relates to compounds according to formula 2 wherein $R^1$ is $CH_2CO_2R^{4a}$, $CH(CO_2R^{4a})CO_2R^{4a}$ or 3 which are useful for the preparation of 1. The 2H-pyridazin-3-one compounds 1 inhibit human immunodeficiency virus (HIV) reverse transcriptase and are useful for treatment of individuals infected with HIV.

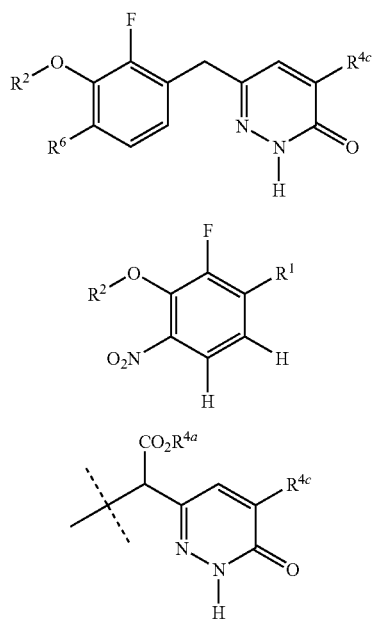

BACKGROUND OF THE INVENTION

Pyridazinones are components of numerous pharmacologically diverse compounds. Thyroxin analogs have been reported, which contain, inter alia, the pyridazinone ring, and these analogs were reported to lower plasma cholesterol without the cardio-stimulatory effect of thyroxine (A. H. Underwood et al. *Nature* 1986 324(6096):425-429; P. D. Leeson et al. *J. Med Chem* 1989 32(2):320-326 and P. D. Leeson et al. EP 0188351). Oxo-pyridazinylmethyl substituted tyrosines that are selective antagonists for the haematopoietic phosphatase SH2 domain have been reported (D. J. Dunnington, WO9624343, WO 9702023 and WO9702024). WO2001085670 (H. Shiohara et al.) discloses related pyridazinone-containing malonamide derivatives useful for treating circulatory diseases. EP 810218 (D. A. Allen et al.) discloses benzoyl substituted benzyl-pyridazinone compounds which are cyclooxygenase inhibitors and potential antiinflammatory or analgesic compounds. U.S. Ser. No. 60/457,144 (J. P. Dunn et al.), hereby incorporated by reference in its entirety, discloses pyridazinone compounds useful to inhibit HIV reverse transcriptase.

The pyridazinone ring can be introduced into a molecule by alkylation of a phenyl acetic acid derivative 4 ($R=CO_2R^{4a}$) or a phenylacetonitrile 4 ($R=CN$) with 3,6-dichloropyrazine (5a; M. M. Rodgers and J. P. English, U.S. Pat. No. 2,371,086). Acid- or based catalyzed hydrolysis of the ester or nitrile 6 ($R=CN$ or $COR^{4a}$) affords the corresponding carboxylic acid which can be isolated if desired, or subjected to acid-catalyzed decarboxylation in situ. Hydrolysis of the chloropyridazine affords the pyridazinone 7. (P. D. Leeson and J. C. Emmett, *J. Chem. Soc. Perkin I* 1988 3085; D. A. Allen et al., EP 810218). While this process is often satisfactory with 5a wherein both chlorine carbon bonds are chemically equivalent, unsymmetrical dichloropyridazinones such as 5b ($R^a$=alkyl) produce a mixture of regioisomers which are often difficult to separate. Alternately, pyridazinones are formally equivalent to 4-oxo-butenoic acid amides and an appropriately substituted 4-oxo-butenoic acid derivative can be converted to pyridazinones by exposure to hydrazine hydrate.

SCHEME 1

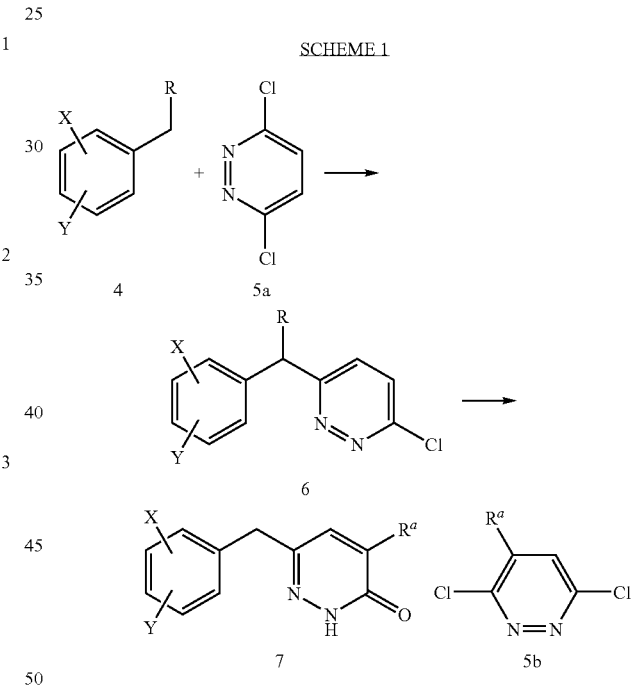

The present process affords a convenient alternate route to 4-alkylpyridazinones 7 (Ra=alkyl) in which the regioisomer problem created by the alkyl substituent is conveniently resolved in an early convergent step in the process. The present invention further affords a convenient route tro 3-(hetero)aryloxy-2-fluoro-phenylacetic acid compounds which are useful intermediates to prepare HIV reverse transcriptase inhibitors. Moreover, the present process permits the regiospecific elaboration of four contiguous aryl carbons.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkenyl" as used herein denotes an unsubstituted hydrocarbon chain radical having from 2 to 10 carbon atoms having one or two double bonds. The term "lower alkenyl" denotes an unsubstituted hydrocarbon chain radical containing 1 to 6 carbon atoms and having one or two double bonds. "$C_{2-10}$ alkenyl" as used herein refers to an alkenyl composed of 2 to 10 carbons. Examples are vinyl, 1-propenyl, 2-propenyl (allyl) or 2-butenyl (crotyl).

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-8}$ cycloalkyl" as used herein refers to an cycloalkyl composed of 3 to 8 carbons in the carbocyclic ring.

The term "alkoxy group" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkylthio" or "thioalkyl" means an —S-alkyl group, wherein alkyl is as defined above such as meththio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an —S-alkyl wherein alkyl is $C_{1-10}$.

The terms "alkylsulfinyl" and "arylsulfinyl" as used herein denotes a group of formula —S(=O)R wherein R is alkyl or aryl respectively and alkyl and aryl are as defined herein The terms "alkylsulfonyl" and "arylsulfonyl" as used herein denotes a group of formula —S(=O)$_2$R wherein R is alkyl or aryl respectively and alkyl and aryl are as defined herein.

The term "haloalkoxy" as used herein denotes a —O-(haloalkyl) group, wherein haloalkyl is as defined herein. Examples of haloalkoxy groups are difluoromethoxy, 2,2,2-trifluoroethoxy, 3-chloropropyloxy. The term "haloalkylthio" as used herein denotes a —S-(haloalkyl) group.

The term "halogen" or "halo" as used herein denotes fluorine, chlorine, bromine, or iodine.

The terms "amino", "alkylamino" and "dialkylamino" as used herein denotes —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)$_n$—, RHN(CH$_2$)$_n$—, and R$_2$N(CH$_2$)$_n$— respectively wherein n is 1 to 6 and R is alkyl as defined above. "$C_{1-10}$ alkylamino" as used herein refers to an-aminoalkyl wherein alkyl is $C_{1-10}$.

The term "acylamino" as used herein denotes a group of formula —NHC(=O)R wherein R is hydrogen, lower alkyl as defined herein.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term "arylcarbonyl" as used herein means a group of formula C(=O)R wherein R is an aryl group; the term "benzoyl" as used herein an "arylcarbonyl" group wherein R is phenyl.

The terms "alkoxycarbonyl" and "aryloxycarbonyl" as used herein denotes a group of formula —C(=O)OR wherein R is alkyl or aryl respectively and alkyl and aryl are as defined herein.

The prefix "carbamoyl" as used herein denotes the radical —CONH$_2$. The prefix "N-alkylcabamoyl" and "N,N-dialkylcarbamoyl" means a the radical CONHR' or CONR'R'' respectively wherein the R' and R'' groups are independently alkyl as defined herein. The prefix N-arylcabamoyl" denotes the radical CONHR' wherein R' is an aryl radical as defined herein.

The term "polar aprotic solvent" means organic solvents such as formamide, N,N-dimethylformamide, dimethylsulfoxide, N-methylpyrrolidone or hexamthylphosphoramide.

The term "ethereal solvent" means solvents such as tetrahydrofuran, dimethoxyethane, dioxane, and dialkyl ethers such as diethyl ether and methyl isobutyl ether.

The term "aryl" as used herein denotes a monovalent aromatic carbocyclic radical containing 5 to 15 carbon atoms consisting of one individual ring, or one or more fused rings in which at least one ring is aromatic in nature, which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, anthraquinolyl tetrahydronaphthyl, 3,4-methylenedioxyphenyl, 1,2,3,4-tetrahydroquinolin-7-yl, 1,2,3,4-tetrahydroisoquinoline-7-yl, and the like. The term "(hetero)aryl" is used to indicate that the ring substituent can be either an aryl or a heteroaryl ring.

The term "aryloxy" as used herein denotes a O-aryl group, wherein aryl is as defined above. An aryloxy group can be unsubstituted or substituted with one or two suitable substituents. The term "phenoxy" refers to an aryloxy group wherein the aryl moiety is a phenyl ring. The term "heteroaryloxy" as used herein means an —O-heteroaryl group, wherein heteroaryl is as defined below. The term "(hetero)aryloxy" is use to indicate the moiety is either an aryloxy or heteroaryloxy group.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyridazinone, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring. The term (hetero)aryl is used to indicate that the ring substituent can be either an aryl or a heteroaryl ring.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "optional" or "optionally" as used herein means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

The term "alkali metal" refers to a group I metal including, but not limited to lithium ($Li^+$), sodium ($Na^+$) or potassium ($K^+$). One skilled in the art will be aware that while these alkali metals are commonly used, other cations such as magnesium ($Mg^{2+}$) may be used without departing from the spirit of the invention.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diethyl iso-propylamine (DEIPA), pyridine (pyr), di-iso-butylaluminumhydride, DIBAL-H, room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

EMBODIMENTS OF THE INVENTION

The present invention affords a process for the preparation of 6-(2-fluoro-3-(hetero)aryloxy-benzyl)-4-alkyl-2H-pyridazin-3-one compounds (8: $R^{4c}$=alkyl) and 6-(2-fluoro-3-(hetero)aryloxy-benzyl)-2H-pyridazin-3-one compounds (8 $R^{4c}$=hydrogen) compounds, wherein $R^1$ and $R^2$ are as defined in claim 1, and said compounds are chemical intermediates useful for the preparation of said pyridazinones. The process exploits the lability of fluorine atoms in trifluoronitrobenzene and results in the regiospecific displacement of two of the three fluorine atoms resulting by the phenoxy moiety and the alkylpyridazinone moiety while retaining a fluorine atom and a nitro group as in 8 (X=$NO_2$). The nitro group can be further reduced to an amine which is further utilized to introduce halogen, alkyl or other substituents into the 4-position. The conversion of an aromatic amine substituent into a variety of other functional groups is well known, e.g., Cl, Br or F, and the preparation of other pyridazinone compounds with other substituents at the 4-position is within the scope of the present invention. A halogen, particularly a bromo or chloro substituent can be converted into the corresponding 4-alkyl substitution by a dialkylzinc in the presence of a palladium catalyst.

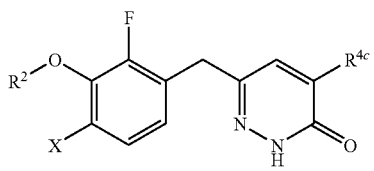

Fluoronitroaromatic compounds are known to be unusually sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amines, thiols and some amides facilely displace fluorine at room temperature (D. Boger et al., *Biorg. Med. Chem. Lett.* 2000 10: 1471-75; F. Terrier *Nucleophilic Aromatic Displacement: The Influence of the Nitro Group* VCH Publishers, New York, N.Y. 1991).

The reaction of sodium methoxide with 2,3,4-trifluoronitrobenzene in methanol has been reported to afford an inseparable mixture of the corresponding 2- and 4-monomethoxy and 2,4-dimethoxy derivatives (P. M. O'Neill et al., *J. Med. Chem.* 1994 37:1362-70). Displacement of the ortho-fluorine of 2,4-difluoronitrobenzene by amine nucleophiles also has been reported. (W. C. Lumma, Jr. et al., *J. Med. Chem.* 1981 24:93-101).

The reaction of 2,3,4-trifluoronitrobenzene (Aldrich catalog No. 33, 836-2) with 3-chloro-5-cyanophenol resulted in regiospecific displacement of the 2-fluoro moiety to afford 9. One skilled in the art will immediately appreciate that although the process is exemplified with 3-chloro-5-cyanophenol, a large number of substituted phenols or hydroxyl substituted heteroaromatic compounds are readily available and could be used to afford many other anti-HIV-compounds.

The displacement reaction can be run in a variety of organic solvents including, but not limited to, ethers (e.g. diethyl ether, THF, DME and dioxane) and alcohols (e.g., iso-propanol and sec-butanol). Solvents capable of directly reacting with the fluoronitrobenzene are clearly precluded as are solvents which may result in the loss of regiochemical control. Thus secondary and tertiary alcohols are acceptable solvents but primary alcohols can displace fluoride. The skilled chemist would be capable of identifying acceptable solvents with minimal experimentation. The phenol is treated with base to afford the phenolate salt. Any alkali metal salt can be employed in the present process but the reaction is conveniently carried out with the lithium, sodium or potassium salts. Sodium phenolates are readily available by treating the phenol with sodium tert-butoxide or sodium tert-amylate in tert-butanol or tert-amyl alcohol respectively. The sodium alcoholate can be prepared by treating the alcohol with sodium metal or sodium hydride. Potassium phenolates can be prepared analogously. Alternatively the phenol can be combined with the sodium alcoholate in THF to afford the salt. The reaction can be run from about −30° C. to about 40° C. without significant loss of the regioselectivity. Typically the reactants are combined at low temperature and allowed to warm to RT after an initial mixing. Under these conditions the aromatic nucleophilic displacement proceeds with high regioselectivity at the 2-position of the substrate

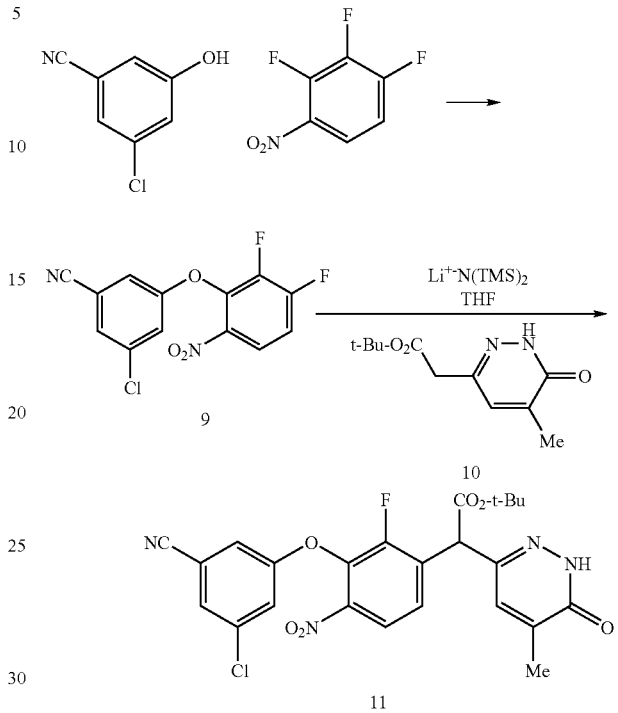

Introduction of the carbon substituent at the 4-position of the benzene ring was achieved by a second subsequent regioselective aromatic nucleophilic displacement with a carbon nucleophile. Suitable carbon nucleophiles are obtained by deprotonation of a carboxylic acid derivative or a malonic acid diester. Deprotonation of a carboxylic acid ester or a nitrile is accomplished with lithium or sodium amide bases such as lithium diisopropylamide, lithium hexamethyldisilazane, lithium diethylamide. Deprotonation also can be effected with sodium or potassium alkoxides or with potassium or sodium hydrides. The deprotonation is generally accomplished in ethereal solvents or polar aprotic solvents at temperatures from about −70° C. to about 0° C. Direct introduction of the pyridazinone is achieved by reacting 9 with (5-methyl-6-oxo-1,6-dihydro-pyridazin-3-yl)-acetic acid tert-butyl ester (10). Advantageously, condensation of 9 and 10 regiospecifically affords the 4-methyl compound and tedious separation of the 4-alkyl and 5-alkylpyridazinone isomers is avoided.

The skilled artisan will comprehend that while use of (hetero)arylacetic acid compounds, such as 10, is sometimes advantageous, the introduction of the (hetero)aryl moiety can also be achieved by a multistep process employing malonic acid diesters. Alkylation of dialkyl malonates, and variations such as mixed diesters, are a fundamental process in organic synthesis and a multitude of variations applicable to the present process have been described (H. O. House, *Modern Synthetic Reactions,* 2 ed., W. A. Benjamin, 1972, New York N.Y., pp. 492-570 and 586-595; W. Carruthers, *Some Modern Methods of Organic Synthesis,* 3rd ed., Cambridge University Press, Cambridge, UK, 1986, pp. 1-26). For example,

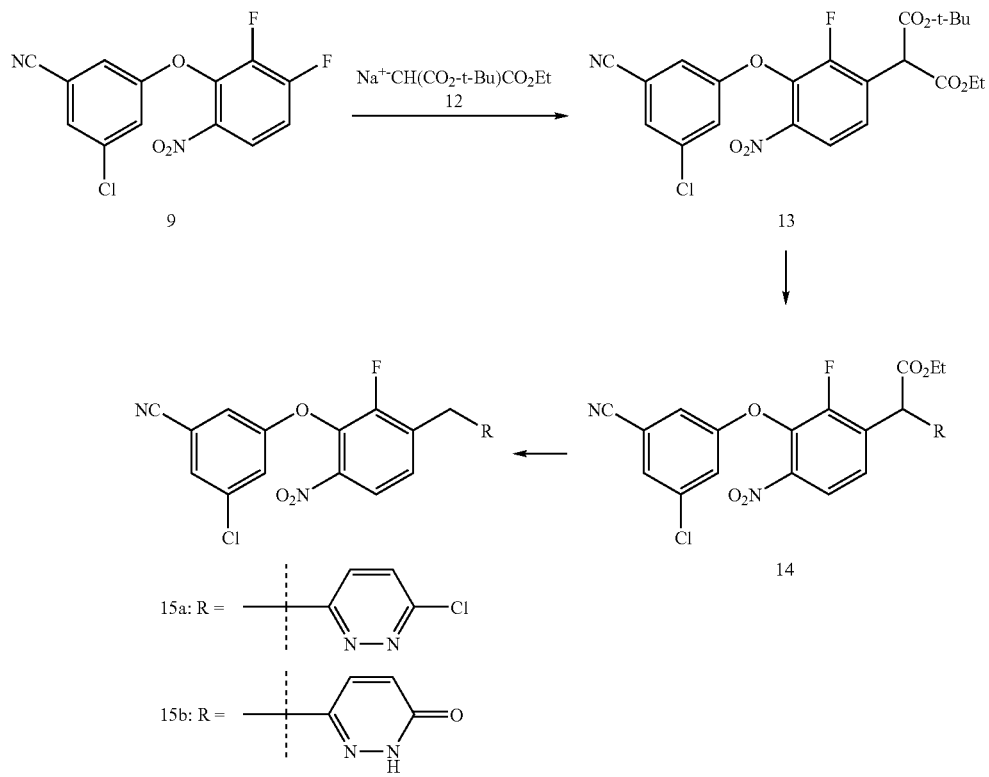

ethyl tert-butyl malonate (12), reacts efficiently with 9 to afford 13. The resulting 3-(phenoxyphenyl)-substituted malonate 13 can be further substituted by a second deprotonation and alkylation or converted to a corresponding phenylacetate (14: R=H) by hydrolysis and decarboxylation. The resulting phenylacetate can, for example, be condensed with 3,6-dichloropyrazine to afford unsubstituted 6-chloropyridazines (15a) which can be converted to the corresponding pyridazinone (15b) by sequential acid hydrolysis and decarboxylation. Considerable flexibility is possible in the sequence of steps and all variations are considered to be within the scope of the invention.

Thus, in one embodiment of the present invention there is provided a process for the preparation

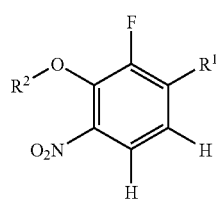

(I)

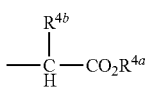

A

-continued

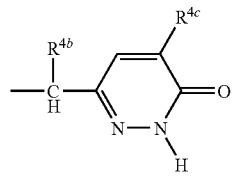

B of a compound according to formula I wherein $R^1$ is A or B; $R^2$ is an aryl radical or a heteroaryl radical wherein said heteroaryl is selected from the group consisting of pyridinyl, pyridine N-oxide, indole, indole N-oxide, pyrimidinyl, pyrazinyl, quinoline, quinoline N-oxide and pyrrolyl; and, said aryl radical and said heteroaryl radical are optionally substituted with zero to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-16}$ alkylamino, $C_{1-16}$ dialkylamino, aminoacyl, acyl, $C_{1-16}$ alkoxycarbonyl, carbamoyl, $C_{1-6}$ N-alkylcarbamoyl, $C_{1-6}$ N,N-dialkylcarbamoyl, nitro and cyano; $R^{4a}$ is hydrogen $C_{1-6}$ alkyl, tert-butyl or benzyl; $R^{4b}$ is hydrogen or —$CO_2R^{4a}$ and, $R^{4c}$ is hydrogen or $C_{1-6}$ alkyl comprising the steps of: (i) contacting an alkali metal (hetero)aryloxide II with 2,3,4-trifluoronitrobenzene in a first solvent at temperatures from about −30° C. up to about 40° C. to afford a 3,4-difluoro-2-(hetero)aryloxynitrobenzene compound III;

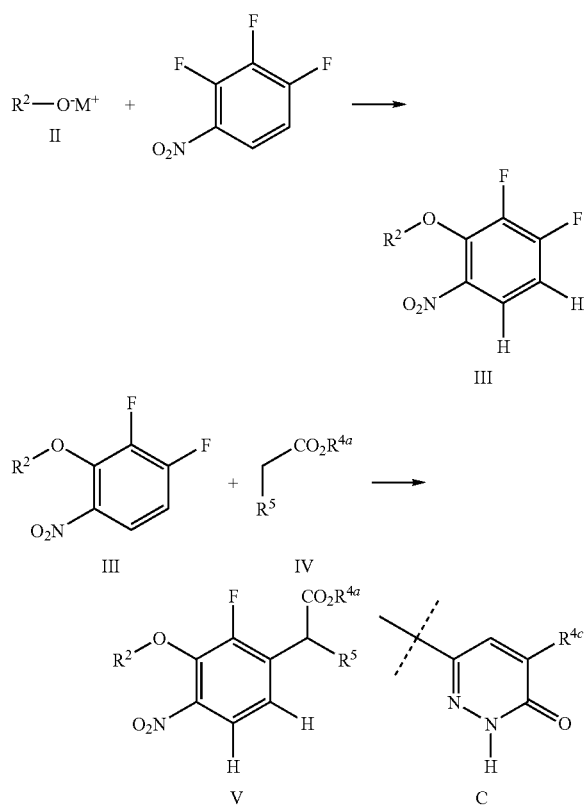

(ii) further contacting said 3,4-difluoro-2-(hetero)aryloxynitrobenzene compound III with alkali metal salt of an acetic acid ester IV wherein $R^5$ is $CO_2R^{5a}$ or C and $R^{5a}$ is independently in each occurence straight or branched $C_{1-6}$ alkyl, in second solvent at a temperature of at least about −78° C. up to about 40° C. to afford a 2-fluoro-3-phenoxyphenylacetic ester V.

Suitable first solvents include, but are not limited to ethereal solvents and secondary and tertiary alcohols. The choice of a suitable base and second solvent will be influenced by the reactants. The second solvent is typically an polar aprotic solvent or an ethereal solvent when strong bases, e.g. alkali metal amides. Aprotic ether solvents may also be used when sodium or potassium alkoxides are used as the base. Alkali metal hydrides are typically used in polar aprotic solvents. The skilled chemist will readily identify suitable combinations of bases and solvents In another embodiment of the present invention there is provided a process for the preparation of a compound according to formula V wherein $R^2$ is 3,5-bis-tert-butylcarbamoylphenyl or 3-chloro-5-cyanophenyl which process comprises (i) contacting an sodium 3,5-bis-tert-butylcarbamoyl-phenolate or sodium 3-chloro-5-cyano-phenolate with 2,3,4-trifluoronitrobenzene in a first solvent at temperatures from about −30° C. up to about 40° C. to afford a 3,4-difluoro-2-(3,5-bis-tert-butylcarbamoyl-phenoxy)nitrobenzene or 3,4-difluoro-2-(3-chloro-5-cyano-phenoxy)nitrobenzene which is further reacted with IV as described below.

In another embodiment of the present invention there is provided a process for the preparation of a compound according to formula III wherein $R^2$ is 3,5-dicyano-phenyl which process further comprises (i) contacting sodium 3,5-bis-tert-butylcarbamoyl-phenolate with 2,3,4-trifluoronitrobenzene in an appropriate solvent at temperatures from about −30° C. up to about 40° C. to afford a 3,4-difluoro-2-(3,5-bis-tert-butylcarbamoyl-phenoxy)nitrobenzene; and (ii) contacting 3,4-difluoro-2-(3,5-bis-tert-butylcarbamoyl-phenoxy)nitrobenzene with phosphorus oxychloride or a similar dehydrating agent to afford 3,4-difluoro-2-(3,5-dicyano-phenoxy) nitrobenzene 111 ($R^2$=3,5-dicyanophenyl). The ether can be convert to IV ($R^2$=3,5-dicyanophenyl) as described below.

In another embodiment of the present invention there is provided a process for the preparation of a compound according to formula VI which process comprises the steps of (i) contacting an alkali metal (hetero)aryloxide II with 2,3,4-trifluoronitrobenzene in a first solvent at temperatures from about −30° C. up to about 40° C. to afford a 3,4-difluoro-2-(hetero) aryloxynitrobenzene compound III; (ii) contacting said 3,4-difluoro-2-(hetero)aryloxynitrobenzene compound III with alkali metal salt of an acetic acid ester IV wherein $R^5$ is $CO_2R^{5a}$ or C and $R^{5a}$ is independently in each occurence straight or branched $C_{1-6}$ alkyl, in a second solvent with a base at a temperature of at least about −78° C. up to about 40° C. to afford a 2-fluoro-3-phenoxyphenylacetic ester V; (iii) hydrolyzing the mono- or di-ester and contacting the resulting mono- or di-acid with acid to afford VI wherein $R^5$ is $CO_2R^{4a}$ or C and $R^{4a}$ or $R^{4c}$ is hydrogen or $C_{1-6}$ alkyl; and, $R^1$, $R^2$ and $R^{4b}$ are as defined in claim 1.

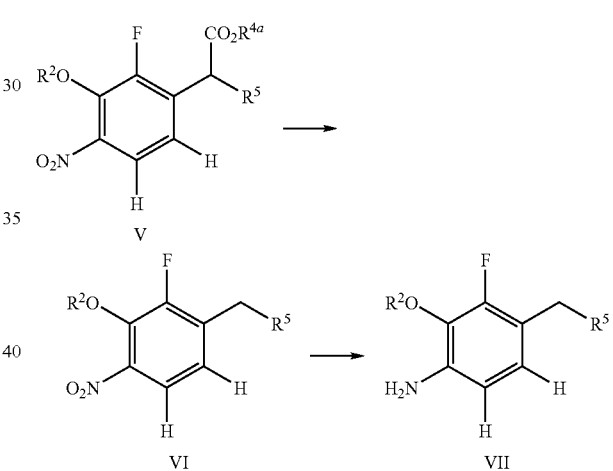

Replacement of the nitro group with other substituents can be achieved by a two-step process comprising reduction of the nitro compound VI to the corresponding amine VII. Reduction of a nitro group to an amine is well known and can be accomplished with inorganic reducing agents, e.g. iron, zinc and tin salts in acidic solvents, or by catalytic hydrogenation. Other conditions which can be employed in the reduction of aromatic nitro groups include $AlH_3$—$AlCl_3$, hydrazine, $TiCl_3$, Al—$NiCl_2$-THF, formic acid and sulfides such as NaHS, $(NH_4)_2S$ or polysulfides. Aromatic nitro compounds have been reduced to amines by $NaBH_4$ in the presence of transition metal catalysts such as $NiCl_2$ or $CoCl_2$. (J. March, *Advanced Organic Chemistry* J. Wiley & Sons, New York, 1992 p 1216-1217).

Aryl chlorides and bromides can be prepared form the corresponding diazonium salt by treating the diazonium salt with cuprous chloride or cuprous bromide (the Sandmeyer Reaction). Aryl diazonium salts are prepared by treating the amine dissolved in dilute mineral acids and cooled to about 0° to about 10° C. with aqueous sodium nitrite. Less reactive weakly basic amines require concentrated acids, e.g. con $H_2SO_4$, or mixtures of con $H_2SO_4$ and glacial acetic acid or phosphoric acid. Fluoroboric acid has also proven useful. An alternate process can be carried out in an organic solvent, e.g., glacial HOAc, MeOH, EtOH, $HCONH_2$, DMF, acetone and others, using nitrite esters, e.g., butyl- or pentyl-nitrite. Other nitrosating agents which can be employed in non-protic solvents include nitrosyl chloride, nitrosyl tetrafluoroborate and the like (K. Schank Synthetic Applications of Diazonium Ions in The Chemistry of the Diazonium and Diazo Group, S. Patai (ed), Part 2, 1978 John Wiley & Sons, New York, N.Y., pp. 647-648.). Aryl chlorides and bromides are formed efficiently by treating the aryl diazonium salt with CuCl or CuBr. A variant of the Sandmeyer procedure uses metallic copper in the presence of hydrochloric or hydrobromic acid (the Gatterman reaction). One-step alternatives two the two step diazotization/Sandmeyer sequence include treating the amine with t-butyl nitrite and cuprous chloride or bromide at elevated temperatures (M. P. Doyle et al. *J. Org. Chem.* 1977 42:2426) or with t-butyl thionitrate and the cuprous halides at room temperature (S. Oae et al. *Bull. Chem. Soc. Japan* 1980 53:1065). Aryl fluorides are accessible from daizonium compounds via the Schiemann Reaction (H. Suschitzky *Adv. Fluorine Chem.* 1965 4:1-30). The Schiemann reaction is carried out by treating a diazonium salt, formed by standard protocols, with $NaBF_4$, $HBF_4$ or $NH_4BF_4$ to form a diazonium tetrafluoroborate salt which can be isolated and thermally converted to the desired aryl fluoride while releasing nitrogen and $BF_3$. Other fluoride salts such as $PF_6^-$, $SbF_6^-$ and $AsF_6^-$ also can be used. Aryl chlorides and bromides are also accessible through the corresponding tetrachloroborate and tetrabromoborate salts (G. Olah and W. S. Tolgyesi *J. Org. Chem.* 1961 26:2053). Aryl iodides are prepared by treating the diazonium salt with iodine.

In another embodiment of the present invention there is provided a process for the preparation of a compound according to formula VII which process comprises the steps of (i) contacting an alkali metal (hetero)aryloxide II with 2,3,4-trifluoronitrobenzene in a first solvent at temperatures from about −30° C. up to about 40° C. to afford a 3,4-difluoro-2-(hetero) aryloxynitrobenzene compound III; (ii) contacting said 3,4-difluoro-2-(hetero)aryloxynitrobenzene compound III with alkali metal salt of an acetic acid ester IV wherein $R^5$ is $CO_2R^{5a}$ or C and $R^{5a}$ is independently in each incidence straight or branched $C_{1-6}$ alkyl, in a second solvent with a base at a temperature of at least about −70° C. up to about 40° C. to afford a 2-fluoro-3-phenoxyphenylacetic ester V; (iii) hydrolyzing the mono- or di- and contacting the resulting mono- or di-acid with acid to afford VI and (iv) contacting VI with a reducing agent to afford amine VII, wherein $R^5$ is $CO_2R^{4a}$ or C and $R^{4a}$ or $R^{4c}$ is hydrogen or $C_{1-6}$ alkyl; and, $R^1$, $R^2$ and $R^{4b}$ are as in claim 1.

In another embodiment of the present invention there is provided a process for the preparation of a compound according to formula VIII (X═Cl or Br) which process comprises the steps of (i) contacting an alkali metal (hetero)aryloxide II with 2,3,4-trifluoronitrobenzene in a first solvent at temperatures from about −30° C. up to about 40° C. to afford a 3,4-difluoro-2-(hetero) aryloxynitrobenzene compound III; (ii) contacting said 3,4-difluoro-2-(hetero)aryloxynitrobenzene compound III with alkali metal salt of an acetic acid ester IV wherein $R^5$ is $CO_2R^{5a}$ or C and $R^{5a}$ is independently in each incidence straight or branched $C_{1-6}$ alkyl, in an aprotic solvent with a base at a temperature of at least about −70° C. up to about 40° C. to afford a 2-fluoro-3-phenoxyphenylacetic ester V; (iii) hydrolyzing the mono- or di-ester and contacting the resulting mono- or di-acid with acid to afford VI; (iv) contacting VI with a reducing agent to afford amine VII; and (v) contacting the amine VII with a diazotizing agent and subsequently contacting the resulting diazonium salt with a cuprous halide to afford VIII, wherein X is chloro or bromo, $R^5$ is $CO_2R^{4a}$ or C and $R^{4a}$ or $R^{4c}$ is hydrogen or $C_{1-6}$ alkyl and $R^1$, $R^2$ and $R^{4b}$ are as defined in claim 1.

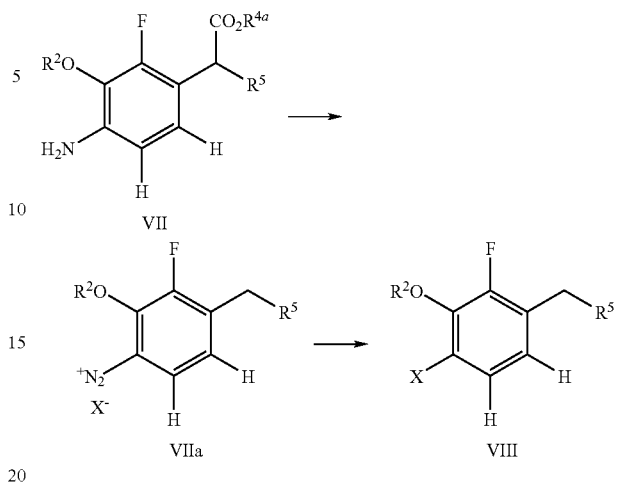

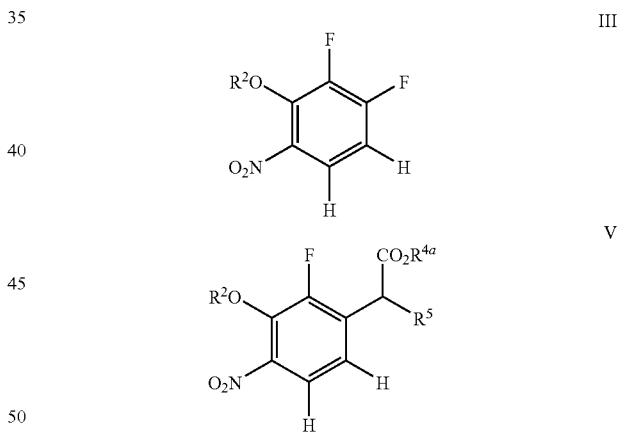

a compound according to formula VIII (X═F) which process comprises the steps of (i) contacting an alkali metal (hetero)aryloxide I with 2,3,4-trifluoronitrobenzene in a first solvent at temperatures from about −30° C. up to about 40° C. to afford a 3,4-difluoro-2-(hetero) aryloxynitrobenzene compound III; (ii) contacting said 3,4-difluoro-2-(hetero)aryloxynitrobenzene compound III with alkali metal salt of an acetic acid ester IV wherein $R^5$ is $CO_2R^{5a}$ or C and $R^{5a}$ is independently in each occurence straight or branched $C_{1-6}$ alkyl, in an aprotic solvent with a base at a temperature of at least about −70° C. up to about 40° C. to afford a 2-fluoro-3-phenoxyphenylacetic ester V; (iii) hydrolyzing the mono- or di-ester and contacting the resulting mono- or di-acid with acid to afford VI; (iv) contacting VI with a reducing agent to afford amine VII; and (v) contacting the amine VII with a diazotizing agent in the presence of a tetrafluoroborate salt or tetrafluoroboric acid and heating said diazonium tetrafluoroborate to afford VIII where X is fluorine, $R^5$ is $CO_2R^{4a}$ or C and $R^{4a}$ or $R^{4c}$ is hydrogen or $C_{1-6}$ alkyl and $R^1$, $R^2$ and $R^{4b}$ are as defined in claim 1.

In another embodiment of the present invention there is provided a process for the preparation of a compound according to formula VIII (X=alkyl) which process comprises the steps of (i) contacting an alkali metal (hetero)aryloxide II with 2,3,4-trifluoronitrobenzene in a first solvent at temperatures from about −30° C. up to about 40° C. to afford a 3,4-difluoro-2-(hetero) aryloxynitrobenzene compound III; (ii) contacting said 3,4-difluoro-2-(hetero)aryloxynitrobenzene compound III with alkali metal salt of an acetic acid ester IV wherein $R^5$ is $CO_2R^{5a}$ or C and $R^{5a}$ is independently in each occurence straight or branched $C_{1-6}$ alkyl, in an aprotic solvent with a base at a temperature of at least about −70° C. up to about 40° C. to afford a 2-fluoro-3-phenoxyphenylacetic ester V; (iii) hydrolyzing the mono- or di-ester and contacting the resulting mono- or di-acid with acid to afford VI; (iv) contacting VI with a reducing agent to afford amine VII; and (v) contacting the amine VII with a diazotizing agent and contacting the diazonium salt with CuBr to afford VIII wherein X is a Br, and (vi) contacting the aryl bromide with a dialkyl zinc Pd(dppf)Cl$_2$ and DIBAL to afford VIII (X=alkyl), wherein $R^5$ is $CO_2R^{4a}$ or C and $R^{4a}$ or $R^{4c}$ is hydrogen or $C_{1-6}$ alkyl and $R^1$, $R^2$ and $R^{4b}$ are as defined in claim 1.

In another embodiment of the present invention there is provided a compound according to formula III wherein $R^2$ is as defined in claim 1.

In another embodiment of the present invention there is provided a compound according to formula V wherein $R^2$, $R^{4a}$, $R^{4c}$ and $R^5$ are as defined in claim 1.

In still another embodiment of the present invention there is provided a compound according to

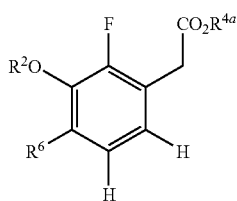

Vb formula Vb wherein $R^2$ is an aryl radical optionally substituted with zero to three substituents independently selected from the group consisting of $C_{1-6}$ alkyl, $C_{1-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, aminoacyl, acyl, $C_{1-6}$ alkoxycarbonyl, carbamoyl, $C_{1-6}$ N-alkylcarbamoyl, $C_{1-6}$ N,N-dialkylcarbamoyl, nitro and cyano;; $R^{4a}$ is hydrogen C1-6 alkyl, tert-butyl or benzyl; and $R^6$ is chloro, bromo or $C_{1-6}$ alkyl.

The pyridazinone 10 was obtained utilizing the Wittig reaction. (see J. W. Schulenberger and S. Archer, *Organic Reactions*, Wiley & Sons, New York 1965 vol. 14, chapter 1, pp. 1-51; J. March, *Advanced Organic Chemistry*, 4$^{th}$ ed., John Wiley & Sons, New York, 1992, pp. 956-963). The phosphorane 16 was condensed with citraconic anhydride 17 which produced an isomeric mixture alkylidene lactones from which the major isomer 18 could be isolated by crystallization (Massy-Westropp, R. A. and Price, M. F., *Aust. J. Chem.* 1980, 33, 333-341). Treating 18 with hydrazine afforded (5-methyl-6-oxo-1,6-dihydro-pyridazin-3-yl)-acetic acid tert-butyl ester (10). The present invention thus provides a convergent synthesis in which separation of the regioisomers is possible on an easily accessible intermediate early in the synthetic sequence.

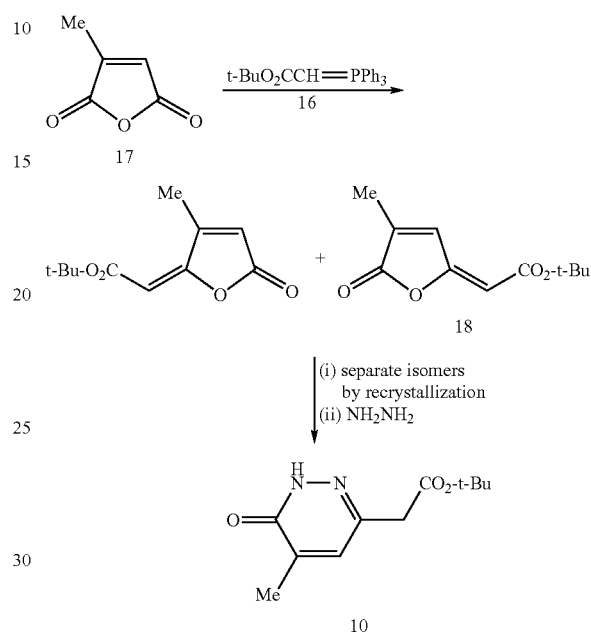

The following examples (infra) are given to enable those skilled in the art to more clearly understand and to practice the present invention. They should not be considered as limiting the scope of the invention, but merely as being illustrative and representative thereof.

EXAMPLE 1

5-[6-Chloro-2-fluoro-3-(5-methyl-6-oxo-1,6-dihydro-pyridazin-3-ylmethyl)-phenoxy]-isophthalonitrile (26)

step 1

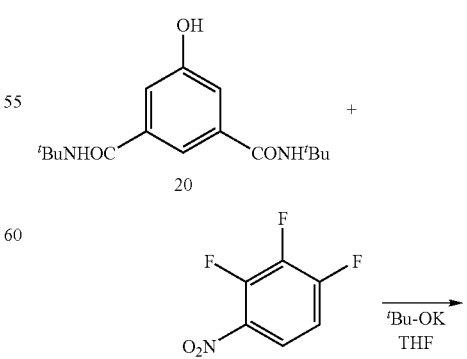

-continued

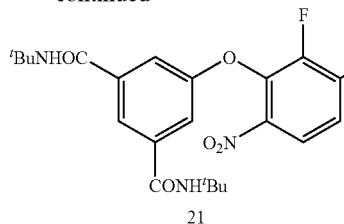

A 22 L round-bottom flask was charged with 3,5-bis-tert-butylcarbamoyl-phenol (20, 360 g, 1.23 mol) and THF (12.5 L). The resulting slurry was cooled to 0° C. and potassium tert-butoxide (1.35 L, 1.0 M in THF, 1.35 mol) was added dropwise over approximately 30 min. After the addition was complete, the reaction mixture was cooled to between −30 and −35° C. and 2,3,4-trifluoronitrobenzene (239, 1.35 mol) was added dropwise over approximately 5 min. The reaction mixture was stirred at approximately −30° C. for 1 h whereupon the cooling bath was removed. The reaction mixture was then stirred for 20 h with warming to ambient temperature. A mixture of water (2.0 L) and brine (1.0 L) was added, and the reaction mixture was stirred vigorously in a 20 L extractor ball. Following removal of the aqueous phase, the organic layer was washed with additional brine (1.5 L), and the resulting THF solution was transferred to a 22 L round bottom flask for distillation. The extractor ball was rinsed with THF (500 mL). After approximately 10 L of THF had been removed by distillation, addition of isopropyl alcohol (11 L) was initiated and the distillation was continued until approximately 23 L of distillate had been collected. When the residual volume was 5 L and the pot temperature was 82° C., water (2.0 L) was added dropwise. Heating was then discontinued, and the reaction mixture was stirred overnight with cooling to room temperature. The resulting solid was filtered through a 3 L course-frit sintered glass filter funnel. The filter cake was washed with IPA/H$_2$O (1:1, 2×600 mL) and dried in a vacuum oven (70° C., 25 Torr) to afford N,N'-di-tert-butyl-5-(2,3-difluoro-6-nitro-phenoxy)-isophthalamide (21; 488 g, 88% theory).

step 2

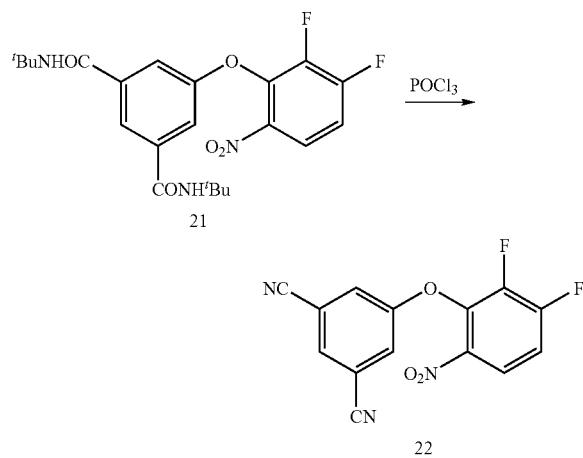

A 5 L round bottom flask was charged with N,N'-di-tert-butyl-5-(2,3-difluoro-6-nitro-phenoxy)-isophthalamide (21; 564 g) and 1.3 L of phosphorus oxychloride. The mixture was heated to between 90° C. and 100° C. for 2 h after which approximately 1/2 of the POCl$_3$ was removed by distillation. Toluene was added (1 L) and additional liquid was distilled. Cooling the mixture overnight and filtering the solid gave crude product. Additional material was obtained by further concentration, treatment with water (2 L) and filtration of the resulting material. The combined solids were stirred in MeOH (0.7 L) for between 1 and 3 h, filtered and dried in a vacuum oven between 50° C. and 80° C. at 25 Torr with a nitrogen bleed to afford 339 g of 22 (90% theory).

step 3

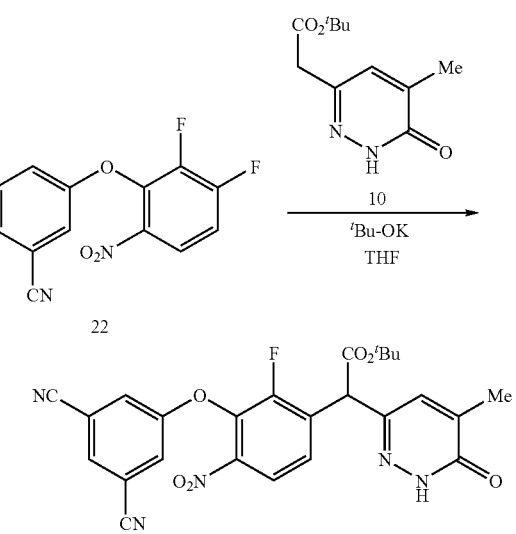

A 5 L three-neck round bottom flask was charged with (5-methyl-6-oxo-1,6-dihydro-pyridazin-3-3-yl)-acetic acid tert-butyl ester (10; 223 g, 0.996 mol) and THF (700 mL). The resulting solution was cooled to 0° C. and potassium tert-butoxide (1.2 L, 1.66 M in THF, 1.99 mol) was added dropwise over approximately 30 min. After cooling the reaction mixture to −55° C., a solution of 5-(2,3-difluoro-6-nitro-phenoxy)-isophthalonitrile (22; 150 g; 0.498 mol) in THF (1.0 L) was added dropwise over approximately 1 h. Following a THF rinse (500 mL), the cooling bath was removed, and the reaction mixture was stirred for 19 h with warming to ambient temperature. The reaction mixture was then quenched by the addition of 1N HCl (1.75 L). Following removal of the aqueous layer (2 L, pH of 3-4) the organic phase was washed with water (1.0 L) and brine (750 mL). The resulting THF solution was filtered through CELITE® and the filter aid washed with THF (500 mL). The solution was then concentrated in vacuo to afford a dark oil which was dissolved in NMP (850 mL) and warmed to approximately 50° C. Water (425 mL) was added dropwise. The cloudy solution was stirred slowly, seeded with a crystal and cooled to 0° C. After stirring at 0° C. for 30 min, the product was filtered. The filter cake was then washed with MeOH (100 mL, 200 mL) and dried in a vacuum oven (50° C., 25 Torr) to afford [3-(3,5-dicyano-phenoxy)-2-fluoro-4-nitro-phenyl]-(5-methyl-6-oxo-1,6-dihydro-pyridazin-3-yl)-acetic acid tert-butyl ester (23; 157 g, 62% theory).

step 4

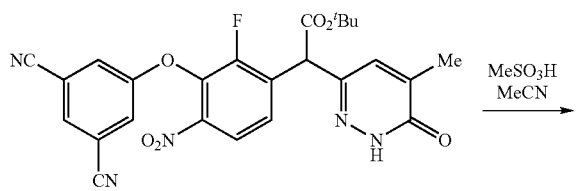

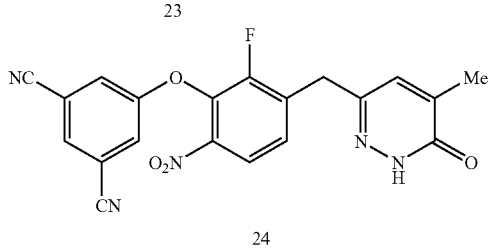

A slurry of 23 (771.1 g), methanesulfonic acid (100 mL) and acetonitrile (1.5 L) was heated to 70° C. under a N₂ atmosphere for 2 h. The solution became homogenous at approximately 52° C. and a solid precipitate reformed after 30 min at 70° C. The reaction mixture was diluted with water (3084 mL) and IPA (3084 µL) and the resulting mixture was aged at 63° C. for 1 h. The heating was stopped and the resulting solution allowed to slowly cool to RT. The solid product was recovered by filtration and the resulting filter cake was thrice washed with H₂O:MeOH (1:1, 500 mL) and dried overnight in a vacuum oven at 80° C. which afforded 24 (603.5 g, 97.6% theory).

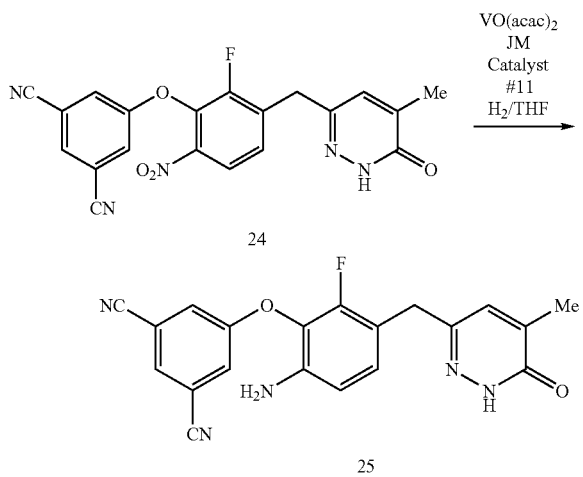

A suspension of 5-[2-fluoro-3-(5-methyl-6-oxo-1,6-dihydro-pyridazin-3-ylmethyl)-6-nitro-phenoxy]-isophthalonitrile (24; 200 g, 0.494 mol) in THF (3.2 L) was warmed to 66° C. to dissolve the solid and the solution was cooled to RT. To resulting solution was added VO(acac)₂ (6.542 g, 24.7 mmol) and 5% palladium (sulfided) on carbon (JM Catalyst # 11; 10.0 g) and the resulting suspension was stirred overnight at RT under a hydrogen atmosphere. The resulting suspension was filtered and the solvent was removed in a rotary evaporator (approximately 2.7 L), a solid precipitate formed and IPA (2.0 L) was added. An additional 600 mL of solvent was removed by evaporation after which the suspension was aged at 40° C. for 5 h and then cooled to RT. The solid was filtered and washed thrice with H₂O:IPA (1:1 v/v, approximately 700 mL). The filtrate and washes were combined and concentrated to afford an additional 23.3 g of product. There was obtained 375.4 g (98% theory) of 5-[6-amino-2-fluoro-3-(5-methyl-6-oxo-1,6-dihydro-pyridazin-3-ylmethyl)-phenoxy]-isophthalonitrile (25).

step 5

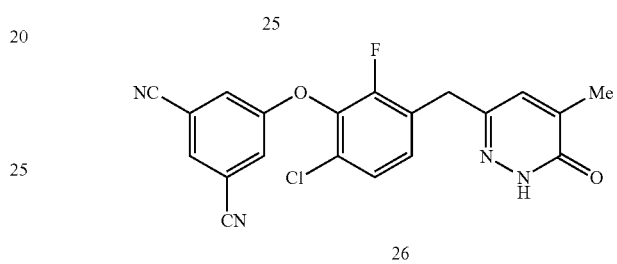

A suspension of 25 (156 g, 0.416 mol) and THF (3.7 L) was heated to reflux to dissolve the amine and approximately 2.3 L of THF was distilled from the solution. A solution of BF₃ etherate (78.3 mL, 88.48 g, 0.623 mol) and 200 mL of THF was cooled to −15° C. The amine solution was pumped into the cooled solution approximately 10 min. The reaction mixture was then maintained at −15° C. for 15 minutes. A solution of tert-butyl nitrite (51.43 g, 0.499 mol) and THF (50 mL) was added over a 5 min period. The cooling bath was removed and the mixture allowed to warm. After 2.5 h the reaction was quenched by the addition of 2.25 L hexane and the resulting solid was stirred and finally filtered. The solid was washed with hexane (4×500 mL) and the resulting solid was dried in a vacuum oven overnight at 30° C. to afford 198 g of the diazonium tetrafluoroborate salt.

CuCl was suspended in MeCN (600 mL) and heated to 65° C. A suspension of the crude diazonium tetrafluoroborate in MeCN (900 mL) was pumped into the cuprous chloride solution over a 10 min period. The pump was washed with MeCN (350 mL). After 1 h at 65° C. the reaction mixture was cooled to about 40° C. and 3M HCl (2.0 L) was added, after which cyclohexane (2.0 L) was added and stirred for 15 min. The resulting precipitate was filtered and washed with water (250 mL) and EtOH (2×400 mL) to afford a light yellow solid which was dried in a vacuum oven at 55° C. to afford 26 (131.6 g, 84.9% theory). An additional 16 g of product was obtained by extracting the aqueous phase with twice with DCM (2.0 L), evaporating the organic phase and chromatographing the resulting oil on silica gel.

3-Chloro-5-[6-chloro-2-fluoro-3-(5-methyl-6-oxo-1,6-dihydro-pyridazin-3-ylmethyl)-phenoxy]-benzonitrile and 3-[6-chloro-2-fluoro-3-(5-methyl-6-oxo-1,6-dihydro-pyridazin-3-ylmethyl)-phenoxy]-5-fluoro-benzonitrile was prepared by an analogous procedure except 3-chloro-5-cyanophenol and 3-cyano-5-fluorophenol respectively were substituted for 20 and the POCl₃ dehydration (step 2) was omitted.

EXAMPLE 2

(5-methyl-6-oxo-1,6-dihydro-pyridazin-3-yl)-acetic acid tert-butyl ester (10)

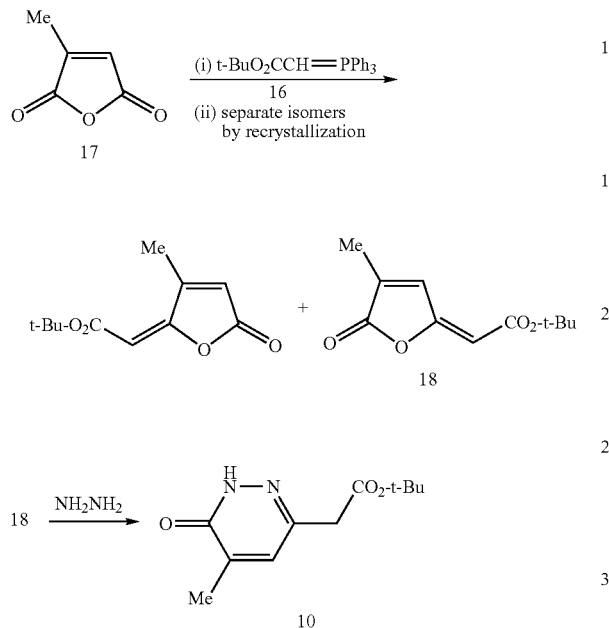

To a cooled (12° C.) solution of the phosphorane (16; 3.008 Kg; 7.99 mol) in THF (12 L) was added citraconic anhydride (1.35 Kg; 12.04 mol) over a 4 h period during which the temperature rose to 35 C. Following the addition, approximately 10 L of THF was removed by distillation and replaced with 4 L of methanol. Addition liquid was removed by distillation and replaced by methanol. A total of 14.6 L was distilled and 7 L of methanol added. To the mixture was added 1 L of water and 6 L of cyclohexane. The cyclohexane layer was separated, and the lower (methanol-water) layer was repeatedly extracted with cyclohexane (a total of 12 extractions each with approximately 6 L of cyclohexane). The cyclohexane fractions were combined and concentrated on a rotary evaporator. After solvent removal, methanol (1 L) was added and the mixture further concentrated on a rotary evaporator. The resulting oil was taken up in methanol (2 L) and cooled to −12° C. for 3 h. After filtration, the solid cake was washed with MeOH (400 mL cooled to 0° C.) and the solid was dried in a vacuum desiccator to afford (4-ethyl-5-oxo-5H-furan-2-ylidene)-acetic acid tert-butyl ester (18, 950 g; 56.6% yield).

To a solution of lactone 18 (2.68 Kg; 12.77 mol) in 7.5 L of NMP cooled to below 0° C. was added 420 mL of anhydrous hydrazine (equivalent quantities of hydrazine hydrate also can be used) while maintaining the internal temperature at less than 20° C. After the addition was completed the reaction mixture was heated to 110-145° C. for one to five h. The reaction mixture was cooled and diluted with H₂O (11 L) which resulted in the formation of crystalline pyridazinone 10 which was filtered and washed with water (2×2 L) and dried to afford 2.23 Kg (77.9%) of product.

EXAMPLE 3

6-[4-Chloro-2-fluoro-3-(1H-indol-7-yloxy)-benzyl]-4-methyl-2H-pyridazin-3-one (31)

step 1

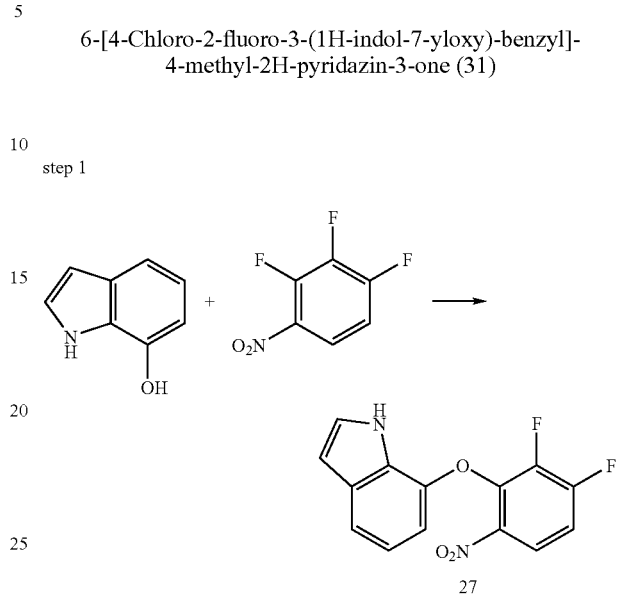

Solid sodium tert-butoxide was added to a ice cold solution of 7-hydroxyindole (1.23 g, 9.24 mmol; *Synthetic Communications* 2003 33:507) in anhydrous THF (145 mL) under a nitrogen atmosphere. The mixture was stirred for 10 min, and 2,3,4-trifluoronitrobenzene (1.06 mL, 9.24 mmol) was added dropwise. The brown solution was stirred for 2 h, and then added to a saturated aqueous solution of NH₄Cl (150 mL). The aqueous layer was extracted with EtOAc (3×100 mL), and the combined organic fractions were washed with H₂O (100 mL), brine (75 mL), and dried over anhydrous MgSO₄. The solvents were evaporated, and the remaining oil was purified by flash chromatography on silica gel (0% to 30% EtOAc/hexanes) to afford 2.26 g (84%) of 27.

step 2

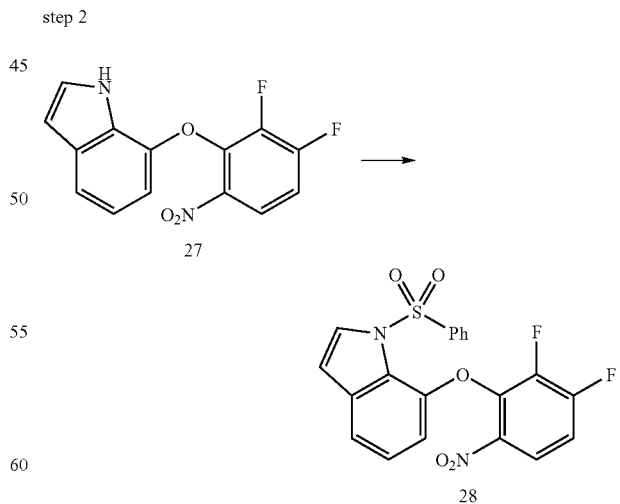

Phenyl sulfonyl chloride (1.05 mL, 8.18 mmol), powdered NaOH (4 g), and Bu₄NHSO₄ (400 mg) were added sequentially to a solution of 27 (2.26 g, 7.79 mmol) in anhydrous CH₂Cl₂ (25 mL). The mixture was stirred for 3 h, and then filtered through CELITE®. The filtrate was washed with H₂O (25 mL), and dried over anhydrous MgSO₄. The solvents were evaporated, and the remaining material was recrystallized from EtOAc. The impure filtrate was purified by column chromatography on silica gel (25% to 40% EtOAc/hexanes), and combined with the crystallized material to afford 2.08 g (62%) of 28.

step 3

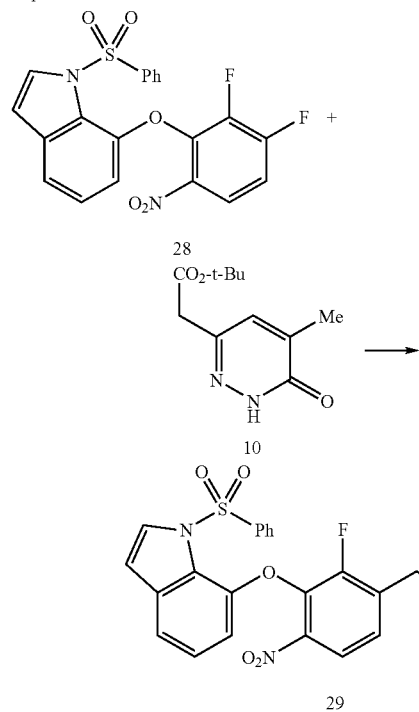

A solution of sodium hexamethyldisilazane (15.5 mL of a 1 M solution in THF, 15.5 mmol) was added slowly to a solution of 28 (2.08 g, 4.83 mmol) and 10 (1.14 g, 5.07 mmol) in anhydrous THF (25 mL) under nitrogen at 0° C. The reaction mixture was stirred for 3 h, and then added to a saturated aqueous solution of NH₄Cl (200 mL). The aqueous mixture was extracted with EtOAc (3×70 mL). The combined organic fractions were then washed with brine (50 mL), and dried over anhydrous MgSO₄. Evaporation of the solvents afforded a red oil which was dissolved in acetic acid (100 mL) and heated to reflux for 5 h. The solvent was removed, and the remaining material was dissolved in EtOAc (100 µL). The organic layer was washed with H₂O (40 mL), brine (25 mL), and dried over anhydrous MgSO₄. The solvents were evaporated and the crude product purified by flash chromatography on silica gel (20% to 100% EtOAc/hexanes) to afford 29 (1.79 g, 69%) as a solid that was only slightly soluble in EtOAc.

step 4

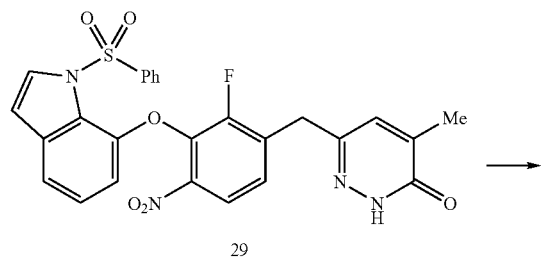

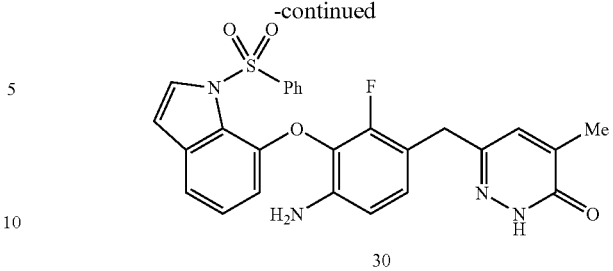

A mixture of pyridazinone 29 (1.79 g, 3.36 mmol), Fe powder (845 mg, 15.12 mmol), and NH₄Cl (809 mg, 15.12 mmol) in EtOH (60 mL) and H₂O (15 mL) was heated to reflux for 3 h. The reaction mixture was cooled to RT and filtered through CELITE®. The filter cake was washed with EtOAc (150 mL), and the combined organic fractions were washed with brine (75 mL), and dried over anhydrous MgSO₄. The solvents were evaporated to provide an oil. The oil was dissolved in CH₂Cl₂ (100 mL), and the organic layer was washed with brine (50 mL), and dried over anhydrous MgSO₄. Evaporation of the solvent provided 30 (1.50 g; 88% theory).

step 5

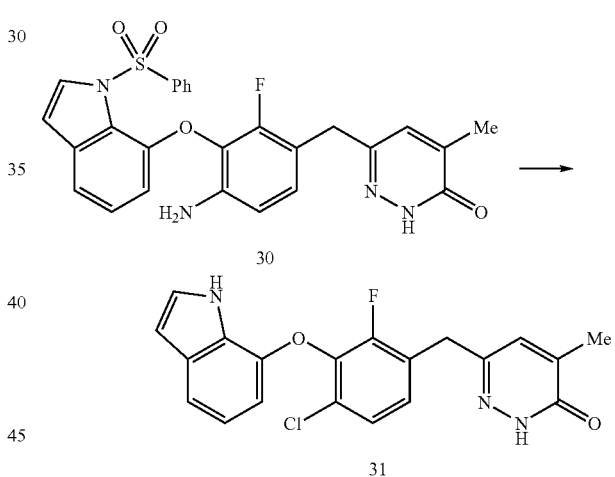

The aniline 30 (700 mg, 1.39 mmol) and CuCl₂ (381 mg, 2.77 mmol) were suspended in anhydrous CH₃CN (14 mL) under a nitrogen atmosphere. tert-Butylnitrite (0.33 mL, 2.77 mmol) was added dropwise, and the reaction mixture was warmed to 60° C. for 1 h. The solution was cooled to RT, and a 5% aqueous HCl solution (20 mL) was added. The layers were separated, and the aqueous layer was extracted with EtOAc (3×30 mL). The combined organic fractions were washed with brine (30 mL) and dried over anhydrous MgSO₄. The solvents were evaporated, and the remaining solid was purified by flash chromatography over silica gel (20% to 100% EtOAc/Hexanes) to provide 500 mg of a solid. The solid was dissolved in anhydrous THF (10 mL) under nitrogen, and TBAF was added dropwise (5.73 mL of a 1.0 M solution, 5.73 mmol). The solution was heated to reflux for 1 h and then cooled to RT. The mixture was quenched with saturated aqueous NaHCO₃, and the aqueous solution was extracted with CH₂Cl₂ (3×30 mL). The combined organic fractions were washed with H₂O (30 mL), brine (30 mL), and dried over anhydrous MgSO₄. The solvents were evaporated, and the remaining solid was purified by repeated flash chromatography on silica gel (1% to 3% MeOH/CH₂Cl₂) to afford 31 (135 mg; 25% theory).

EXAMPLE 4

6-[3-(5-bromo-1-oxy-pyridin-3-yloxy)-4-chloro-2-fluoro-benzyl]-4-methyl-2H-pyridazin-3-one (41)

step 1

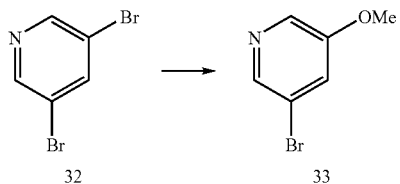

A solution of 3,5-dibromopyridine (32, 20 g, 84.4 mmol) in DMF (200 mL) was stirred at RT under nitrogen atmosphere and 21.3 mL of sodium methoxide (25% by wt. in methanol, 92.8 mmol) was added slowly. The reaction mixture was stirred overnight at 70° C. under N₂. The reaction was cooled to RT and quenched with water (200 mL) and extracted with Et₂O (2×200 mL). The combined organic extracts was washed with brine, dried (MgSO₄) and concentrated in vacuo. The crude 3-bromo-5-methoxypyridine (33, 14.8 g, 93% theory) afforded a colorless oil after flash chromatography on silica gel (EtOAc:hexane 1:10).

step 2

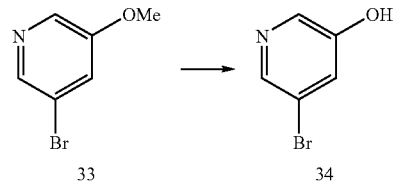

A solution of 3-bromo-5-methoxy-pyridine (33 18.8 g, 0.1 mol), HBr (80 mL, 48%) and glacial HOAc (60 mL) was stirred overnight at 120° C. Hydrobromic acid (60 mL, 48%) was added slowly to replace evaporated solvents and stirred at 120° C. for overnight. The reaction mixture was cooled to RT and then poured into the ice. The pH was adjusted to about 6 by adding 6N NaOH and then extracted with EtOAc (2×200 mL). The organic layer was dried over Na₂SO₄ and concentrated in vacuo. The crude product was stirred in CH₂Cl₂ (150 mL) and the resulting precipitate was filtered. The product was washed with CH₂Cl₂ to afford 3-bromo-5-hydroxypyridine (34; 15.2 g, 87.4% theory) as a white solid.

step 3

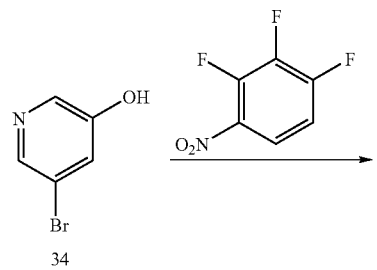

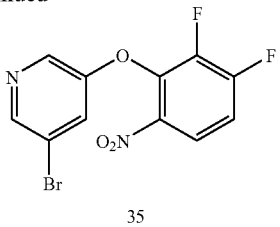

A solution of 3-bromo-5-hydroxypyridine (34, 7.4 g, 42.5 mmol) in anhydrous THF (40 mL) was stirred at 0° C. under Ar atmosphere and potassium tert-butoxide (46.8 mL, 1 M solution in THF) was added slowly. After 1 h at 0° C., 2,3,4-trifluoronitrobenzene (7.91 g, 44.6 mmol) in 15 mL of THF was added very slowly. The reaction mixture was stirred at RT for 2 h, quenched with water (80 mL) and extracted with EtOAc (2×80 mL). The combined organic extracts were dried (MgSO₄) and concentrated in vacuo. The crude product was purified by flash chromatography on silica gel (EtOAc:hexane 1:15) to afford 35 (11 g, 78%) as a light orange oil.

step 4

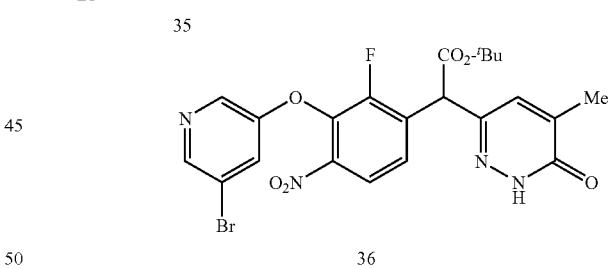

A solution of (5-methyl-6-oxo-1,6-dihydro-pyridazin-3-yl)-acetic acid tert-butyl ester (10, 7.1 g, 31.7 mmol) and 35 (11 g, 33.3 mmol) in anhydrous THF (30 mL) was stirred at −78° C. under an Ar atmosphere and 112 mL of LiHMDS (1.0M solution in THF) was added very slowly. The reaction mixture was stirred in the cold bath (dry-ice/IPA) for 3 h then in an ice bath for 2 h. The reaction was quenched with a solution of NaHSO₄·H₂O (5% by wt) and extracted with EtOAc (2×100 mL). The combined organic extracts were dried (MgSO₄) and concentrated in vacuo. The product was isolated by a flash chromatography on silica gel (EtOAc: hexane 1:2 to 2:1) to afford 36 as a yellow solid (10.2 g, 60% yield).

step 5

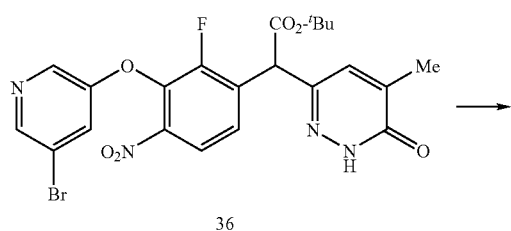

36

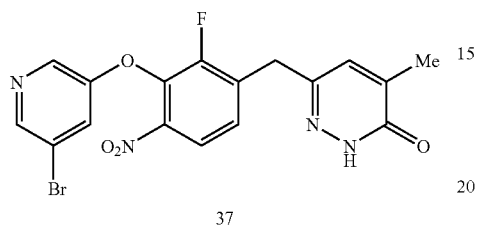

37

A solution of 36 (10.2 g, 19.1 mmol) in HOAc (120 mL) under a nitrogen atmosphere was heated to reflux overnight. It was cooled to RT and the HOAc was evaporated in vacuo. A saturated NaHCO₃ solution (70 mL) was added and the aqueous mixture extracted with EtOAc (2×80 mL). The combined organic fractions were dried (MgSO₄) and concentrated in vacuo. The crude product was isolated by a flash chromatography. on silica gel (EtOAc:hexane 1:2 to 2:1) to afford 37 as a light yellow solid (4.6 g, 55.3% theory): ms (M+H)⁺=436.

step 6

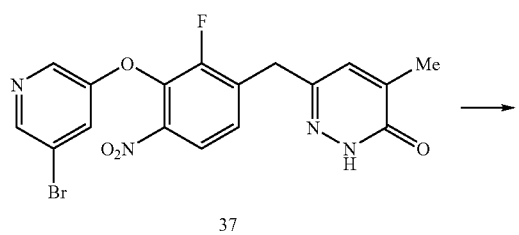

37

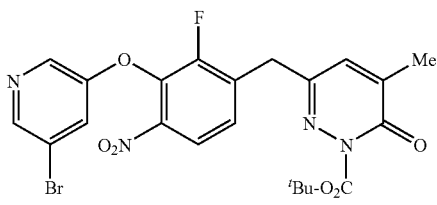

38

A solution of 37 (1.8 g, 4.4 mmol), di-tert-butyl dicarbonate (1.16 g, 5.3 mmol), and 4-dimethylaminopyridine (0.2 g) in anhydrous THF (30 mL) was maintained under an Ar atmosphere and stirred at RT overnight. The reaction mixture was quenched with water and extracted with EtOAc (2×30 mL). The combined organic fractions were dried (MgSO₄) and concentrated in vacuo. The product was isolated by a flash chromatography on silica gel (1:10 to 2:1 EtOAc:hexane) to afford 38 as a white solid compound (0.85 g; 38% theory).

step 7

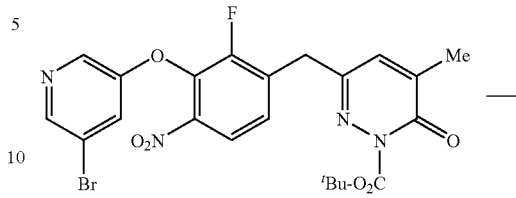

38

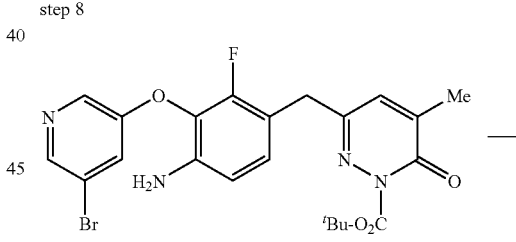

39

To a solution of 38 (4 g; 9.19 mmol) in absolute EtOH (60 mL) was added NH₄Cl (0.984 g, 18.40 mmol) dissolved in water (10 mL). The resulting mixture was heated at 60° C. until the reaction was homogeneous. Fe(0) (0.77 g, 13.78 mmol) was then added and the mixture stirred vigorously at 60° C. for 6 h. When reduction was complete the hot reaction mixture was filtered through a pad of CELITE® which subsequently was washed with hot EtOAc. The resulting filtrated was cooled and extracted with EtOAc and the combined extracts washed sequentially with water and brine. The EtOAc extract was dried (Na₂SO₄), filtered and the volatile solvent was removed in vacuo to afford a pale orange oil which was recrystallized from hexanes to yield 39 (1.8 g, 48.3% theory).

step 8

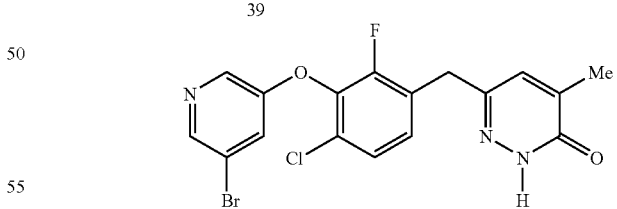

39

40

Aniline 39 (0.85 g, 1.69 mmol) and CuCl₂ (575 mg, 3.37 mmol) were suspended in anhydrous CH₃CN (20 mL) under a nitrogen atmosphere. tert-Butyl nitrite (0.348 g, 3.37 mmol) was added dropwise, and the reaction mixture was warmed to 60° C. for 1 h. The solution was cooled to RT, and a 5% aqueous HCl solution (20 mL) was added. The layers were separated, and the aqueous layer was extracted with EtOAc (3×30 mL). The combined organic fractions were washed with brine (30 mL) and dried over anhydrous MgSO₄. The solvents were evaporated, and the remaining solid was purified by flash chromatography over silica gel (20% to 100% EtOAc/hexanes) to provide 500 mg of a solid. The solid was dissolved in anhydrous DME (10 mL) and TFA (1 mL) was added. The solution was stirred at RT for 1 h. The mixture was quenched with saturated aqueous NaHCO₃, and the aqueous solution was extracted with CH₂Cl₂ (3×30 mL). The combined organic fractions were washed with H₂O (30 mL), brine (30 mL), and dried over anhydrous MgSO₄. The solvents were evaporated, and the remaining solid was purified by repeated flash chromatography on silica gel (1% to 3% MeOH/CH₂Cl₂) to afford 40 (290 mg; 49.9% theory; mp 184.9-188° C., ms [M+H]⁺=424).

step 9

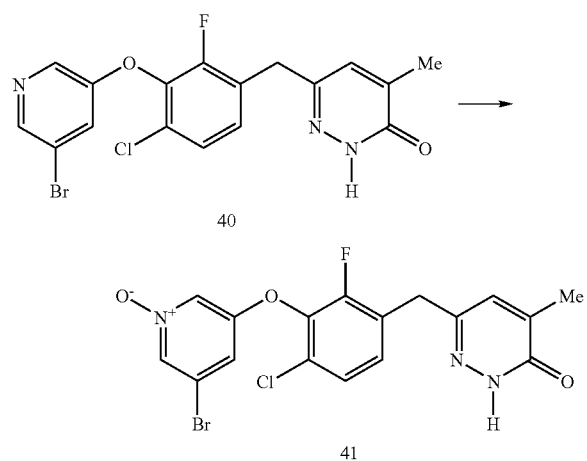

A solution of the pyridine 40 (0.2 g, 0.47 mmol) and MCPBA (0.09 g, 0.52 mmol) in anhydrous chloroform (10 mL) was heated at reflux for 6 hours. The reaction mixture was cooled to RT, and diluted with 0.05N NaOH (5 mL) and extracted with chloroform (2×10 mL). The combined organic fractions were dried (MgSO₄) and concentrated in vacuo. The crude product was purified by a flash chromatography on silica gel (MeOH:CH₂Cl₂ 0.1 to 1:10) to afford 6-[3-(5-bromo-1-oxy-pyridin-3-yloxy)-4-chloro-2-fluoro-benzyl]-4-methyl-2H-pyridazin-3-one (41, 60 mg; 32% theory) as a white solid: mp 197.9-198.9° C., ms (M+H)⁺=440.

EXAMPLE 5 step 1

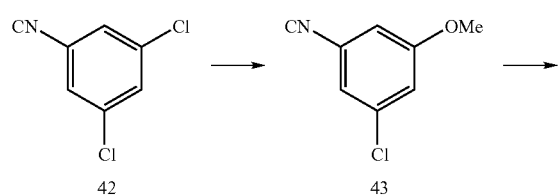

-continued

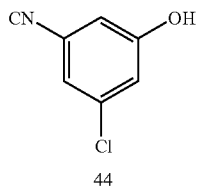

To a 250 mL round bottom flask charged with 3,5-dichlorobenzonitrile (42; 7.31 g; 34.90 mmol) and maintained under an argon atmosphere was added DMF (70 mL). The flask was cooled to 0° C. and powdered sodium methoxide (1.88 g; 34.90 mmol) was added in two portions 15 min apart. The homogeneous mixture was allowed to warm to room temperature and stirred for 24 h. The solution was cooled to 0° C. and aqueous 10% HCl (20 mL) was added dropwise via an addition funnel after which the reaction was warmed to RT. The mixture was extracted with EtOAc and the combined extracts washed sequentially with water and brine. The organic phase was dried (Na₂SO₄), filtered, and volatile solvents were removed in vacuo. The resulting solid was recrystallized from hexanes to afford 3-chloro-5-methoxybenzonitrile (43, 4.2 g; 72%).

A 250 mL round bottom flask was charged with 43 (4.2 g; 25.05 mmol) and 2,4,6-collidine (60 mL) was added. The mixture was stirred under an argon atmosphere until the solution was homogeneous. Anhydrous lithium iodide (10.06 g; 75.18 mmol) was added and the mixture was heated to 175° C. for 3 h. The reaction mixture was cooled to RT and partitioned between 10% HCl and EtOAc. The EtOAc phase was washed sequentially with 10% HCl and brine, dried (Na₂SO₄), filtered and evaporated in vacuo to afford a oil which was crystallized from hexanes to afford 3-chloro-5-hydroxybenzonitrile (44, 3.5 g, 91% theory).

step 2

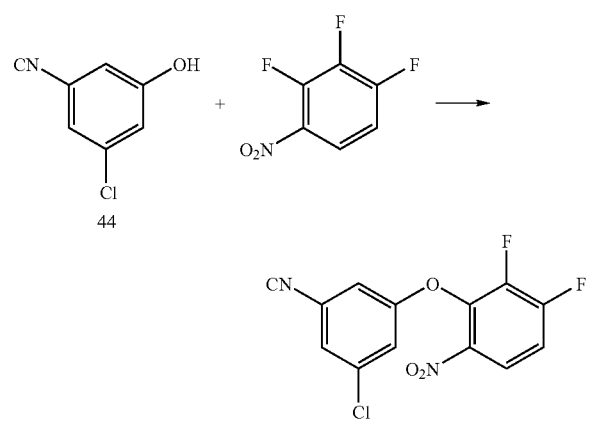

To an ice-cold solution of 3-chloro-5-hydroxybenzonitrile (44; 3.5 g; 22.80 mmol) and dry THF (50 mL) maintained under an argon atmosphere was added sodium tert-butoxide (2.2 g; 22.80 mmol) in two portions 15 min apart. The reaction mixture was stirred until the mixture was homogeneous. To the ice-cold solution was added dropwise 2,3,4-trifluoronitrobenzene (4.0 g; 22.80 mmol) over 30 min. The reaction was stirred at 0° C. for 3 h and then allowed to warm to RT. The reaction was cooled to 0° C. and quenched by addition of 10% HCl via addition funnel. The resulting mixture was extracted with EtOAc and the combined organic phases washed sequentially with 10% HCl and brine. The EtOAc was dried (Na$_2$SO$_4$), filtered and the volatile solvent removed in vacuo to yield a yellow oil which was crystallized from hexanes to yield 45 (6.3 g, 89% theory)

The resulting solution was extracted with EtOAc and washed sequentially with saturated NaHCO$_3$, water and brine. The organic phase was dried (Na$_2$SO$_4$), filter and the volatile solvents removed in vacuo. The resulting dark oil was crystallized from hexanes to afford 47 (6.5 g, 92% theory).

step 3

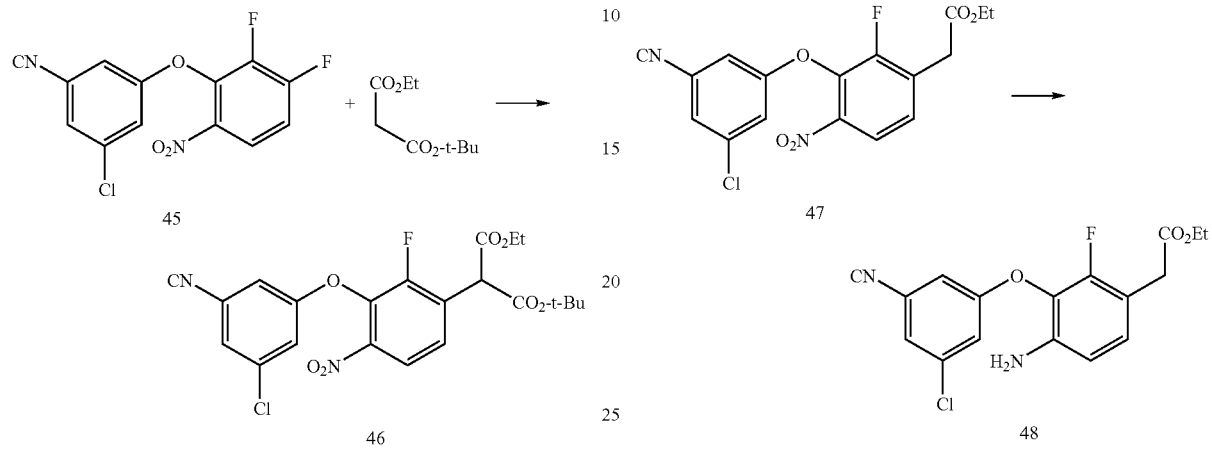

step 5

To an ice-cold solution of tert-butyl ethyl malonate (3.8 g; 20.28 mmol) and dry NMP maintained under an argon atmosphere was added NaH (1.2 g, 48.67 mmol, 60% in mineral oil) over a 45 min interval. The reaction was stirred for an additional 30 min after which 45 (6.3 g, 20.28 mmol) was added dropwise and the resulting solution stirred for 4 h. The reaction mixture was cooled to 0° C. and quenched by dropwise addition of a saturated NaHSO$_4$ solution. The mixture was extracted with EtOAc and the combined organic extracts washed sequentially with water and brine. The EtOAc solution was dried (Na$_2$SO$_4$), filtered and the volatile solvents removed in vacuo to afford 46 as a purple oil that was used without further purification.

To a solution of 47 (6.5 g; 17.20 mmol) and absolute EtOH (100 mL) was added NH$_4$Cl (1.84 g, 34.39 mmol) dissolved in water (20 mL). The resulting mixture was heated at 60° C. until the reaction was homogeneous. Fe(0) (1.44 g, 25.80 mmol) was then added and the mixture stirred vigorously at 60° C. for 6 h. When reduction was complete the hot reaction mixture was filtered through a pad of CELITE® which subsequently was washed with hot EtOAc. The resulting filtrate was cooled and extracted with EtOAc and the combined extracts washed sequentially with water and brine. The EtOAc extract was dried (Na$_2$SO$_4$), filtered and the volatile solvent was removed in vacuo to afford a pale orange oil which was crystallized from hexanes to yield 48 (5.0 g, 83% theory).

Introduction of 5-bromo Substituent step 4

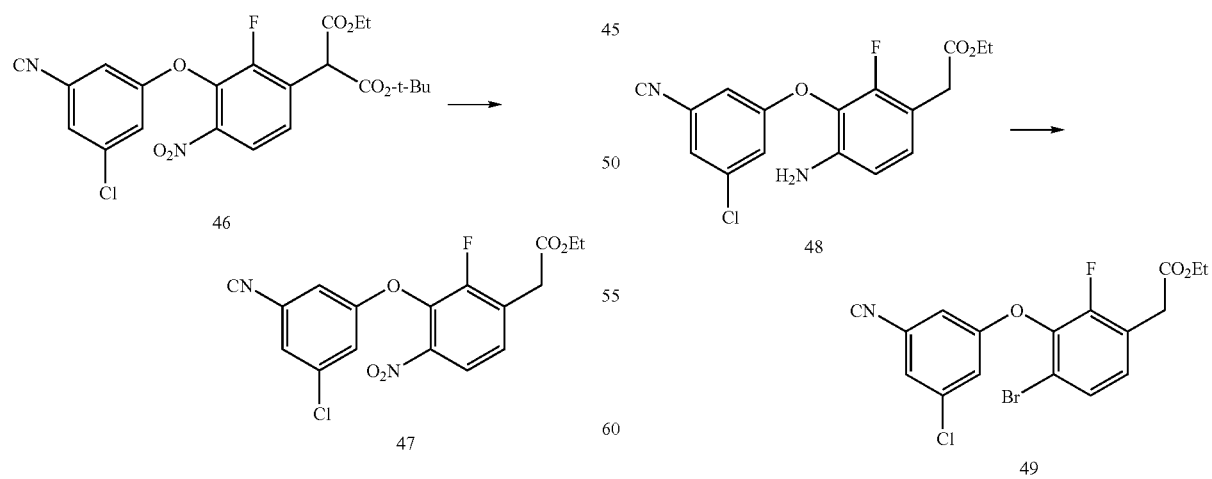

The crude mixed ester 46 from the previous step (8.9 g; 18.60 mmol) was dissolved in DCM (100 mL) and 50 mL of TFA was added and the solution was to heated to 60° C. for 24 h. The reaction mixture was cooled to 0° C. and saturated NaHCO$_3$ was added dropwise to the stirred reaction mixture.

A 150 mL three-neck round bottom flask was charged with MeCN (50 mL), CuBr (2.8 g, 12.61 mmol) and t-butyl nitrite (1.4 g, 13.76 mmol), degassed and maintained under an Ar atmosphere and heated to 70° C. To the mixture was added dropwise a solution of 48 (4.0 g, 11.47 mmol) dissolved MeCN (20 mL). The reaction mixture was stirred at 70° C. for 4 h and then cooled to 0° C. The reaction was quenched by addition of 10% HCl (30 mL) and extracted with EtOAc. The combined extracts were sequentially washed with 10% HCl and brine. The organic extract was dried (Na2SO4), filtered and the volatile solvents removed in vacuo to yield a black oil which was purified by flash chromatography on silica gel (hexanes:EtOAc 95:5) to afford 49 (2.5 g, 52.8% theory).

Introduction of 5-methyl Substituent

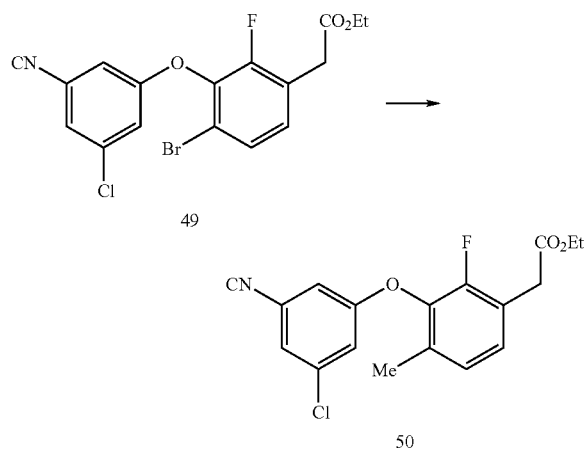

To a degassed ice-cold solution of THF (15 mL), Pd(dppf)Cl$_2$ (0.09 g, 0.121 mmol) was added DIBAL-H (0.012 mmol; 1M in toluene). The reaction mixture was allowed to warm to RT. A solution of 49 (1.0 g, 2.42 mmol) was added followed by dimethyl zinc (1M in THF, 4.240 mmol). The reaction was heated to 65° C. for 4 h, cooled to RT and quenched with aqueous NH$_4$Cl. The resulting mixture was extracted with EtOAc and washed sequentially with NH$_4$Cl and brine. The EtOAc extract was dried (Na$_2$SO$_4$), filtered and the volatile solvent removed in vacuo to yield a dark brown oil that was purified by flash chromatography on silica gel (hexanes: EtOAc 95:5) to yield 50 (0.50 g, 59% theory).

Introduction of 5-ethyl Substituent

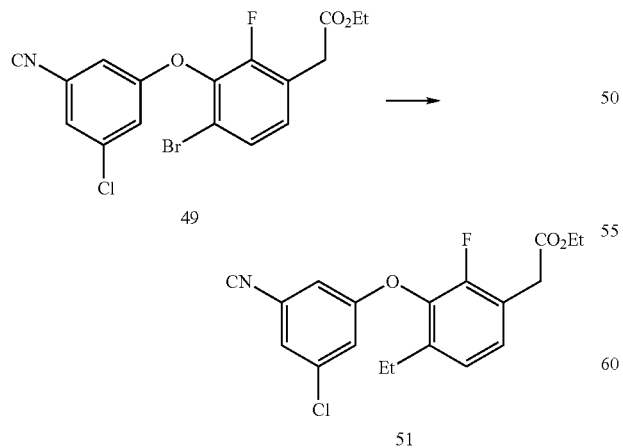

51 was prepared in by an identical procedure to 50 except diethylzinc was substituted for dimethyl zinc. The product was purified by flash chromatography on silica gel (hexanes: EtOAc 95:5) to yield 49 (0.65 g, 74% theory).

Introduction of a pyridazinone into 49, 50 or 51 is carried out by the deprotonation of the phenylacetic acid and condensation with 3,6-dichloropyrazine as described in U.S. Ser. No. 10/807,993 (J. P. Dunn et al., U.S. Publication 20040198736.).

[4-Chloro-3-(3-cyano-5-difluoromethyl-phenoxy)-2-fluoro-phenyl]-acetic acid ethyl ester, [4-Bromo-3-(3-cyano-5-difluoromethyl-phenoxy)-2-fluoro-phenyl]-acetic acid ethyl ester, [3-(3-cyano-5-difluoromethyl-phenoxy)-2-fluoro-4-methyl-phenyl]-acetic acid ethyl ester and [3-(3-cyano-5-difluoromethyl-phenoxy)-4-ethyl-2-fluoro-phenyl]-acetic acid ethyl ester were prepared by a similar route except in step 2,3-chloro, 5-hydroxy benzonitrile was replaced with 3-difluoromethyl-5-hydroxy-benzonitrile. These compounds are useful synthetic intermediates for the synthesis of pyridazinone compounds.

The features disclosed in the foregoing description, or the following claims expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula Va wherein:

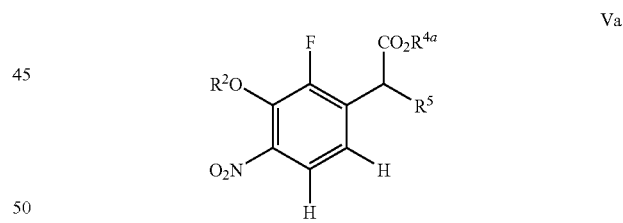

R$^2$ is an aryl radical and said aryl radical is optionally substituted with zero to three substituents independently selected from the group consisting of C$_{1-6}$ alkyl, C$_{1-6}$ alkenyl, C$_{1-6}$ haloalkyl, C$_{3-8}$ cycloalkyl, C$_{1-6}$ alkoxy, C$_{1-6}$ alkylthio, C$_{1-6}$ alkylsulfinyl, C$_{1-6}$ sulfonyl, C$_{1-6}$ haloalkoxy, C$_{1-6}$ haloalkylthio, hydroxyl, halogen, amino, C$_{1-6}$ alkylamino, C$_{1-6}$ dialkylamino, C$_{1-6}$ N,N-dialkylcarbamoyl, nitro and cyano;

R$^{4a}$ is in each occurrence is independently hydrogen, C$_{1-6}$ alkyl or benzyl;

R$^5$ is H or CO$_2$R$^{5a}$: and

R$^{5a}$ is independently in each occurrence a straight or branched C$_{1-6}$ alkyl.

* * * * *